United States Patent
Link (10) Patent No.: US 8,740,986 B2
(45) Date of Patent: Jun. 3, 2014

(54) FINGER JOINT PROSTHESIS

(75) Inventor: Helmut Link, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 104 days.

(21) Appl. No.: 13/181,857

(22) Filed: Jul. 13, 2011

(65) Prior Publication Data
US 2012/0016484 A1     Jan. 19, 2012

(30) Foreign Application Priority Data
Jul. 14, 2010   (DE) .......... 10 2010 031 349

(51) Int. Cl.
*A61F 2/42*     (2006.01)

(52) U.S. Cl.
USPC ..................................... 623/21.15

(58) Field of Classification Search
USPC ..................................... 623/21.15
See application file for complete search history.

(56) References Cited

U.S. PATENT DOCUMENTS

| | | | | |
|---|---|---|---|---|
| 5,443,516 | A * | 8/1995 | Albrektsson et al. | 623/23.39 |
| 5,984,970 | A * | 11/1999 | Bramlet | 623/21.15 |
| 2010/0057214 | A1* | 3/2010 | Graham et al. | 623/21.15 |
| 2010/0082112 | A1 | 4/2010 | Keller et al. | |

FOREIGN PATENT DOCUMENTS

| | | | |
|---|---|---|---|
| DE | 69002159 T2 | 10/1993 | |
| DE | 102007008406 A1 | 8/2008 | |
| EP | 1096906 A1 | 5/2001 | |
| ES | 2209489 T3 * | 6/2004 | ............... A61F 2/42 |
| WO | 9011739 A1 | 10/1990 | |
| WO | 00/04850 A1 | 2/2000 | |

OTHER PUBLICATIONS

Int'l Search Report issued Oct. 13, 2011 in Int'l Application No. PCT/EP2011/062000: Written Opinion.
Office Action issued Mar. 9, 2011 in DE Application No. 102010031349.1.

* cited by examiner

*Primary Examiner* — Bruce E Snow
*Assistant Examiner* — Melissa Hoban
(74) *Attorney, Agent, or Firm* — Panitch Schwarze Belisario & Nadel LLP (57) ABSTRACT

A finger joint prosthesis includes a joint body 14 having first and second joint elements pivotably connected about an axis of rotation and anchoring bars 30, 32 extend from the joint body for securing to a proximal and a distal phalanx. The anchoring bars 30, 32 include one or more securing eyes 40, 42, 44 with openings for receiving fixing screws therein. To provide improved primary and secondary fixing, an end securing element is provided distally from the axis of rotation on the anchoring bar 30, 32 of at least one joint element.

9 Claims, 6 Drawing Sheets

FINGER JOINT PROSTHESIS

BACKGROUND OF THE INVENTION

The present invention concerns a finger joint prosthesis generally including a joint body having first and second joint elements. The joint elements are preferably connected together pivotably about an axis of rotation, and each joint element preferably includes an elongate anchoring bar for implementing a secondary securing to a proximal and/or distal phalanx. In addition, one or more eyes having openings for receiving fixing screws for implementing a primary fixing can also be provided on the anchoring bars. The fixing screws provide for primary fixing for fixing the prosthesis in the target position on the bones. The finger joint prosthesis then grows to the bone in the context of the biological or secondary fixing in the bone. Secondary fixing is then effected by way of the surface of the finger joint prosthesis.

Functional disorders of finger middle joints can occur on the one hand by virtue of an inherited degenerative illness, joint arthrosis. In that case, the illness leads to "wear" of the joint cartilage and consequently corresponding inappropriate stresses with complete changes in the joint surfaces which result in painful limitation or even seizure of the joint function. On the other hand, functional disorders in the finger middle joint can also occur because of injury, for example, due to luxation of the joint or due to a joint fracture. Primary treatment of a joint fracture generally leads to a so-called "post-traumatic arthrosis" of the joint, which also leads to a painful functional limitation or functional immobilization of the finger middle joint.

One way of eliminating the above-indicated functional disorders is to stiffen the joint in a position which is favorable to its function. That way admittedly results in freedom from pain but it means that the joint becomes completely inoperable.

For implantation of earlier finger joint prosthesis, the inner collateral ligament had to be detached at the phalanx for ulnar access. The joint was then laterally luxated and a part of the palmar plate detached. The head of the first phalanx and the base of the second phalanx were then resectioned in such a way that a previously determined spacing resulted between the two phalanges. Thereupon a rectangular space extending along the center line of each phalanx was produced by a rasp in each phalanx. A shaft guide was then cemented into that rectangular space. The joint elements were then individually fitted with their anchoring bars into the shaft guide, the phalanges were bent back and the first and second joint elements were hingedly connected together by inserting a spindle into the aligned openings.

As the finger middle joint had to be laterally luxated upon implantation of the known finger joint prostheses the extensor tendon assembly, the two flexor tendons and the collateral ligaments of the joint were irritated, which resulted in later impairment of operability of the joint. In addition a large amount of bone substance was sacrificed for implantation of the finger joint prosthesis, as a shaft guide had to be inserted in the direction of the center line of the finger joints. DE 690 02 159 discloses such a prosthesis in which, in accordance with the description, a reduced loss of bone substance is to be encountered upon implantation.

A markedly improved finger joint prosthesis is known from EP 1 096 906 to the inventor Christoph Ranft. That permits a novel and improved method while avoiding the above-mentioned disadvantages. In the method described in EP 1 096 906, the finger joints prosthesis can be implanted in the assembled condition radially into a pre-prepared bore in the finger joint, which represents a marked simplification in installation and leads to slight injuries, in particular at the tendons of the finger.

On the other hand that finger joint prosthesis is of an excessively filigree structure and has a partial lack of strength and durability. DE 10 2007 008 406 discloses a radially implantable finger joint prosthesis which enjoys a higher degree of stability but which at the same time can still be easily implanted with slight injury to the patient. In accordance with DE 10 2007 008 406 that object is attained in that the first joint element has an outside hollow body having an insertion opening, the second joint element has an inside hollow body, the inside hollow body can be inserted relatively into the outside hollow body in the installation position by way of the insertion opening and a spindle can be fitted into the inside hollow body in the installation position for rotatable connection to the outside hollow body.

Although the prosthesis disclosed in DE 10 2007 008 406 has stability which is considerably improved over the state of the art, there are nonetheless certain weaknesses in anchorage, in particular in relation to loadings arising out of a distal pull. That can lead to loosening of the finger joint prosthesis, in particular on the distal anchoring bar. In that way the prosthesis can grow into place in an unwanted position. In addition growth (secondary fixing) can be delayed or be entirely absent.

BRIEF SUMMARY OF THE INVENTION

Accordingly, an objective of a preferred embodiment of the present invention is to further develop a finger joint prosthesis as set forth in the opening part of this specification in such a way that the aforementioned disadvantages, and in particular the problem of distal loosening are at least partially avoided and consequently providing a finger joint prosthesis having improved primary and secondary fixing.

According to a preferred embodiment of the present invention, the above objective is attained in that, in a finger joint prosthesis of the kind set forth in the opening part of this specification, there is provided an end securing element distally from the axis of rotation on the anchoring bar of at least one joint element.

In that respect it has proven to be particularly advantageous if the end securing element is arranged medially in relation to the horizontal central plane of the anchoring bar. In that arrangement the central plane should extend parallel to the plane defined by the flat anchoring bar. The center point of the end securing element is then therefore on the horizontal central plane of an anchoring bar. That means that the end securing element is arranged medially and explicitly not laterally in relation to the central plane of the anchoring bar. Advantageously, it would be possible in that way for lateral, proximal securing elements such as for example eyes to be supplemented and/or entirely or partially replaced.

The configuration of such an end securing element has the advantage over the structure set forth in DE 10 2007 008 406 that, in the configurations of the end securing element according to a preferred embodiment of the present invention, the prosthesis permits stronger anchoring, even in relation to loadings arising out of a distal pull and permits in particular improved growth to the bone. Fixing can also be effected medially in relation to the center line of the finger. It is thus possible to particularly well counteract the aforementioned problems arising in the state of the art, in particular in relation to unwanted lever effects. The invention makes it possible to implement improved primary and secondary fixing. Loosening of the finger joint prosthesis, in particular on the distal anchoring bar, can thus be prevented and the consequences thereof can be avoided. That effect is afforded inter alia by virtue of the fact that better engagement of the securing elements into the medial corticalis and into the spongy region is allowed. Unfavorable lever effects are avoided by the end arrangement of the securing element and at the same time the surface area of the prosthesis is increased. It was found in the development of a preferred embodiment of the present invention that the problems in the state of the art are caused inter alia by the fixing of the finger joint prosthesis at the radial attachment of the finger outside the center line of the finger. That problem is avoided or reduced by a preferred embodiment of the present invention.

The end securing element can be provided on the finger for securing the finger joint prosthesis, in widely varying ways, for example by the securing element being in the form of an end securing eye. In that case the end securing eye can also be arranged medially in relation to the horizontal central plane of the anchoring bar. That eye which is preferably arranged in one piece in the extent of the anchoring bar is adapted to carry tensile forces. That specific arrangement has the advantage over the known structure that there is no need to provide a recess in the respective anchoring bar to permit it to be even inclinedly screwed into the bone. The increase in surface area in the anchoring bar, which is thus afforded, also permits improved growth to the bone and stronger anchoring. As no recesses have to be provided in the surface of the anchoring bar the configuration of the anchoring bar can be more filigree or can be better adapted to the geometry of the finger; in that way for example it is possible to dispense with a front-end projection in the joint region to compensate for the notch effect of a recess. That also provides better engagement of the screw means into the spongy region and into the medial corticalis. The end arrangement of the screw means reduces disadvantageous lever forces and provides a better hold against laterally breaking out.

The end securing element can for example also comprise two adjacent end eyes. That additional fixing additionally reinforces anchoring of the prosthesis and permits it to better grow into place.

It has been found to be particularly desirable for the end securing element to be in the form of a cylinder extending along the width of the anchoring bar. Such a cylinder can be "wedged" in the bone and thus provides a stronger anchoring in relation to loads, including a distil pull. At the same time the increase in surface area due to the cylinder permits improved growth to the bone. The end arrangement of the cylinder reduces unfavorable lever effects and engages into the spongy region and into the medial corticalis. The cylindrical shape is also advantageous for the reason that the corresponding recess in the bone can be produced by mere drilling instead of complicated and expensive milling. It is particularly preferred for the cylinder to be also arranged medially on the horizontal central plane of the anchoring bar.

The surface of the end securing element and/or the entire finger joint prosthesis can additionally be of a rough nature to promote improved growth to the bone.

It will be appreciated that it is also in accordance with a preferred embodiment of the present invention for the two above-described and further preferred embodiments of the end securing element to be combined.

For, it will be appreciated that the geometry of the end securing element does not amount to nothing more than being in the form of an eye or cylinder, but rather it is possible to envisage further configurations which are adapted to even better carry tensile forces and permit improved growth and improved anchoring.

An interponate can be provided for bridging over major tissue damage. Such an interponate can be particularly simply in the form of a "place holder" in the form of a polished cylinder. The dimensions of the cylinder correspond in diameter and length to the existing finger joint or any other joint. In order also to avoid injury the cylinder after implantation should not protrude medially or laterally. In addition the outside region of the cylinder should be rounded off. In that sense it is also desirable if all edges can be harmonically adapted to the respective bone. Cobalt-chromium-molybdenum alloys (CoCrMo) as well as titanium with a titanium-niobium coating are particularly suitable as materials for the interponate. The described characteristics of the interponate can be similarly transferred, as far as appropriate, to all conceivable configurations of the end securing element and further components of the finger joint prosthesis according to the invention.

It is also possible to use a hinge in which the first joint element has an outside hollow body with an insertion opening, the second hinge element has an inside hollow body, the inside hollow body can be inserted relatively into the outside hollow body in the installation position by way of the insertion opening, and a spindle can be inserted into the inside hollow body in the installation position for rotatable connection to the outside hollow body. Both the outside hollow body and also the inside hollow body are provided with an outside peripheral surface and an inside peripheral surface respectively. The outside peripheral surface of the inside hollow body is slightly smaller than the inside peripheral surface of the outside hollow body so that the inside hollow body in the position of installation can be relatively movably inserted into the outside hollow body. Both the outside hollow body and also the inside hollow body are of a rotationally symmetrical configuration and are of the same geometry to ensure trouble-free rotation.

In the particularly preferred embodiment of the hinge the outside hollow body and the inside hollow body are in the form of hollow cylinders.

It has proven to be particularly advantageous for the outside hollow body and the inside hollow body to be made from metal as metal enjoys high stability and fatigue strength for in vivo use. In that respect titanium has particularly good sliding and friction properties, in which respect titanium nitrite is particularly preferably used, being biocompatible and having a particularly good abrasion performance. It will be appreciated that the same also applies to the entire finger joint prosthesis according to the invention.

If the hollow bodies are made from metal the spindle can be of plastic material as that forms a particularly good material pairing with hollow bodies. The use of polyethylene (PE) is particularly preferred. It is, however, in accordance with a preferred embodiment of the present invention for the spindle also to be made from a metal.

To reduce the frictional forces between the end faces of the inside hollow body and the outside hollow body, plastic disks can be inserted between the end faces of the inside hollow body and the outside hollow body, such disks preferably also comprising polyethylene (PE).

The finger joint prosthesis according to a preferred embodiment of the present invention can preferably be used for a proximal interphalangeal joint (PIP joint) and can carry the forces occurring at that joint without any problem. To provide for the desired force-carrying capability the outside diameter of the outside hollow body is between about 1.5 and 2 times as large as the outside diameter of the spindle. In the case of a PIP joint the outside hollow body is preferably of an outside diameter of 12 mm and the spindle is of an outside diameter of 6 mm. Use as a replacement for a distal interphalangeal joint (DIP joint) or possibly also as a metacarpophalangeal joint (MCP joint) is however also within the scope of the invention. In principle the structure according to the present invention can also be implemented for other joints when involving correspondingly different dimensioning, but while retaining the advantageous size relationships described hereinbefore.

Abutment means can be provided between the outside and inside hollow bodies, which limit the angle of rotation to a predetermined amount. In the particularly preferred embodiment the abutment means are in the form of shoulders at the outer peripheral surface of the inside hollow body, which in the installation position butt against the edges of the insertion opening of the outside hollow body. Preferably the angle of rotation is between 0 and 135 degrees, particularly preferably between 0 and 90 degrees.

A plurality of tap-like recesses can also be provided on the anchoring bar. The recesses are preferably arranged on the anchoring bar in relation to lateral proximal securing eyes in such a way as also to permit the fixing screws to be inclinedly screwed in. As the aforementioned securing eyes are arranged on the anchoring bar between the axis of rotation and the remote end the fixing screws would collide with the anchoring bar when being screwed in, without recesses. To prevent that, slope portions can also be provided on the anchoring bar. The securing eyes are preferably inclined slightly with respect to the vertical so that an acute angle is included between the eye and the surface of the plane of the anchoring bar.

While in the state of the art such recesses were necessary on the front and/or rear side of the anchoring bar as only lateral securing eyes are provided, it is possible to entirely or partially dispense with recesses by virtue of the end securing element according to the invention. In the above-described fashion that increases the surface area of the anchoring bar, increases the freedom in terms of design in relation to the anchoring bar, provides for stronger anchoring and permits improved growth to the bone.

For better primary fixing, one or more ribs can be provided on the anchoring bars, which preferably extend perpendicularly to the center line of the finger on the top side and/or underside of the anchoring bars, to permit the finger joint prosthesis to be radially pushed into the bone. The ribs can be of a polygonal and/or rounded configuration in cross-section. Preferred cross-sections are for example triangular, rectangular or in the form of a semicircle. The ribs can be provided on a flat side or also at both sides of an anchoring bar. The increase in surface area of the anchoring bar, afforded by the ribs, prevents displacement, improves growth to the bone and thus permits an improvement in fixing of the prosthesis. Preferably those ribs narrow towards the side of the anchoring bar which engages into the spongy region. That facilitates radial insertion of the finger joint prosthesis upon being fitted into the finger bone.

The securing elements of the finger joint prosthesis can also include exclusively distal end securing elements, in particular the end securing eyes. With that configuration, recesses for inclined screwing do not have to be provided whereby the stability of the anchoring bars is considerably improved in comparison with the aforementioned structures, because of the absence of a notch effect. That structure also improves growth to the bone because the surface area of the anchoring bars is increased.

Furthermore the end securing element according to a preferred embodiment of the present invention, in accordance with a special shape, can be in the form of a wing-like horizontal widening of the distal anchoring bar. The widening is preferably perpendicular to the axis of the finger joint. The horizontal wing-like securing element preferably extends from the distal end of the anchoring bar to a recess on the same anchoring bar. The end of the wing-like widening, that engages into the spongy bone, is preferably formed with a narrowing. That facilitates insertion of the finger joint prosthesis upon installation. The narrowing can be for example in the form of a rounded configuration. That also has the advantage that the matched recess in the bone then does not have any corners or the like which in known manner can promote cracking or fracture in the bone. In that way growth to the bone and the load-bearing capability of the finger joint prosthesis can be improved. Furthermore the above-mentioned recess can be particularly easily provided with a circular saw or the like. It is possible to avoid complicated and expensive milling.

The wing-like end securing element which in the installation position extends at least over the center line of the finger joint, preferably approximately as far as the length of the axis of the finger joint, means that detrimental lever effects in the anchoring bar can be reduced. It is thus possible to avoid fractures caused by material fatigue of the finger joint prosthesis, which can occur in particular in the region of the recesses.

Hitherto the attempt was made to counteract fractures by widening the surface of the anchoring bar. That widening was mostly provided on the anchoring bar in such a way that in the installation position it protruded in the form of a forwardly projecting projection or "hump" over the respective finger bones, also to be able to radially insert the finger joint prosthesis into the bone. The wing-like widening towards the biomechanical finger center line means that such widenings of the surface are not necessary to achieve the required stability. The design configuration of the anchoring bars can now be better adapted to the respective bone. It is thus also possible to avoid injury to the soft tissues by projecting parts of the finger joint prosthesis.

In abstracted terms the invention concerns a finger joint prosthesis comprising a joint body having first and second joint elements which are connected together pivotably about an axis of rotation and from which a respective anchoring bar extends for securing to a proximal and/or distal phalanx, wherein the anchoring bars can have one or more securing eyes with openings for receiving fixing screws and which to avoid the aforementioned disadvantages has an end securing element distally from the axis of rotation on the anchoring bar of at least one joint element.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Certain terminology is used in the following description for convenience only and is not limiting. The words "top," "front" and "rear" designate directions in the drawings to which reference is made. The word "outwardly" refers to a direction away from the geometric center of the joint or device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Figure 1:
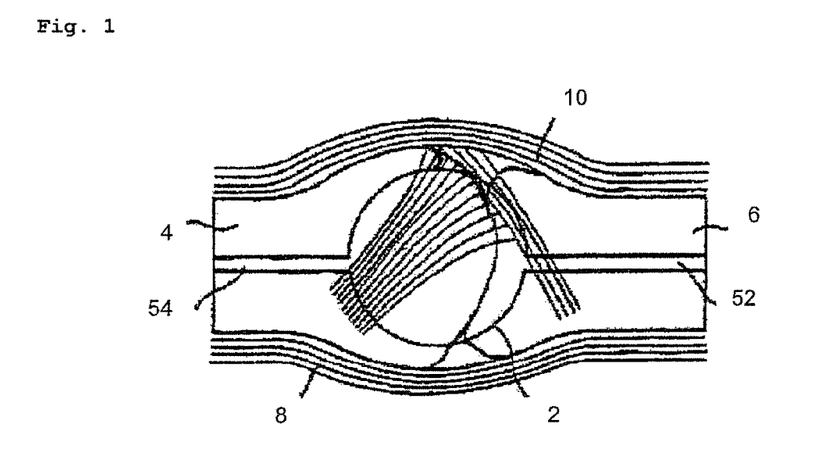
FIG. 1 is a diagrammatic radial view of a finger middle joint indicating the location for implantation of a finger joint prosthesis according to a preferred embodiment of the present invention.

FIG. 1 shows the radial side of a finger middle joint 2 with a proximal phalanx 4, that is proximal or nearer to the body, and a distal phalanx 6, that is distal or remote from the body. An extensor tendon 8 is shown below the phalanx and a flexor tendon 10 is shown above the finger middle joint.

The finger joint prosthesis shown in FIGS. 2-5 serves for radial implantation in the finger joint shown in FIG. 1 at the portion of the hinge joint indicated by the circle in the middle of FIG. 1.

Figure 2:
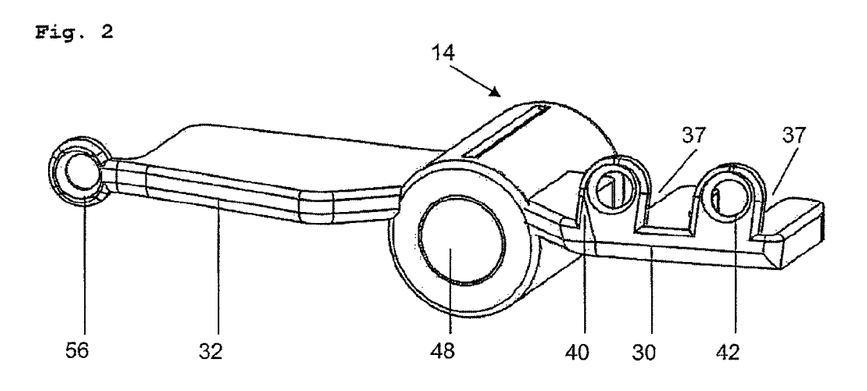
FIG. 2 is a perspective view of the finger joint prosthesis according to a first preferred embodiment of the present invention, wherein an end securing element being in the form of a securing eye on a distal anchoring bar.

FIG. 2 shows a perspective view of a preferred embodiment of the assembled finger joint prosthesis. The assembled finger joint prosthesis has a joint body 14 which preferably includes a first joint element having a proximal anchoring bar 30 and a second joint element having a distal anchoring bar 32, which are hingedly connected together so that the second joint element is pivotable about an axis A (see FIG. 5) with respect to the first joint element. Provided at the end of the distal anchoring bar 32 is a medial securing eye 56. The proximal anchoring bar 30 has lateral proximal securing eyes 40, 42 and corresponding recesses 37.

Figure 3:
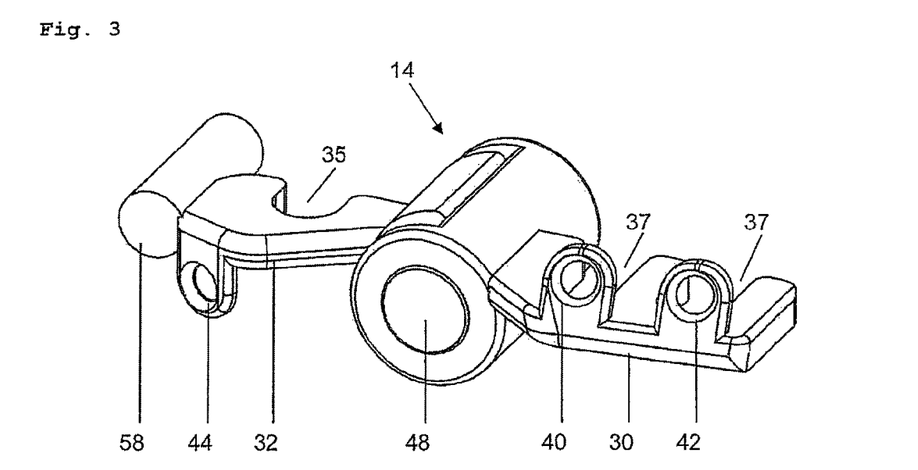
FIG. 3 is a perspective view of a finger joint prosthesis according to a second preferred embodiment of the present invention, wherein the end securing element being in the form of a cylinder on the distal anchoring bar.

FIG. 3 shows a perspective view of a further configuration of the assembled finger joint prosthesis. The end securing element is here in the form of a cylinder 58 and is disposed on the distal anchoring bar 32. The assembled finger joint prosthesis further has a lateral proximal securing eye 44. The configuration of the proximal anchoring bar 30 corresponds to that in FIG. 2.

Figure 4:
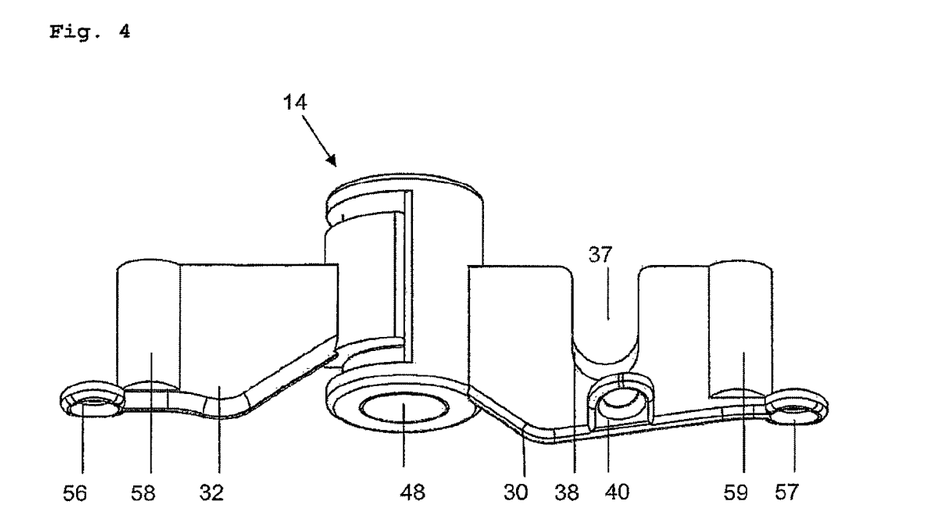
FIG. 4 is a plan view of a finger joint prosthesis according to a third preferred embodiment of the present invention with a combination of an end cylinder and an end securing eye for the distal and proximal anchoring bars.

FIG. 4 shows a plan view illustrating the implantation position of an assembled finger joint prosthesis, wherein the end securing element according to a preferred embodiment of the invention is provided at the ends, remote from the axis A, of the distal and proximal anchoring bars 32, 30. In this case, the structures shown in FIGS. 2 and 3 have been combined. The distal anchoring bar 32 has a securing eye 56 and a cylinder 58. The proximal anchoring bar 30, besides a lateral proximal securing eye 40, has the cylinder 59 and the securing eye 57.

Figure 5:
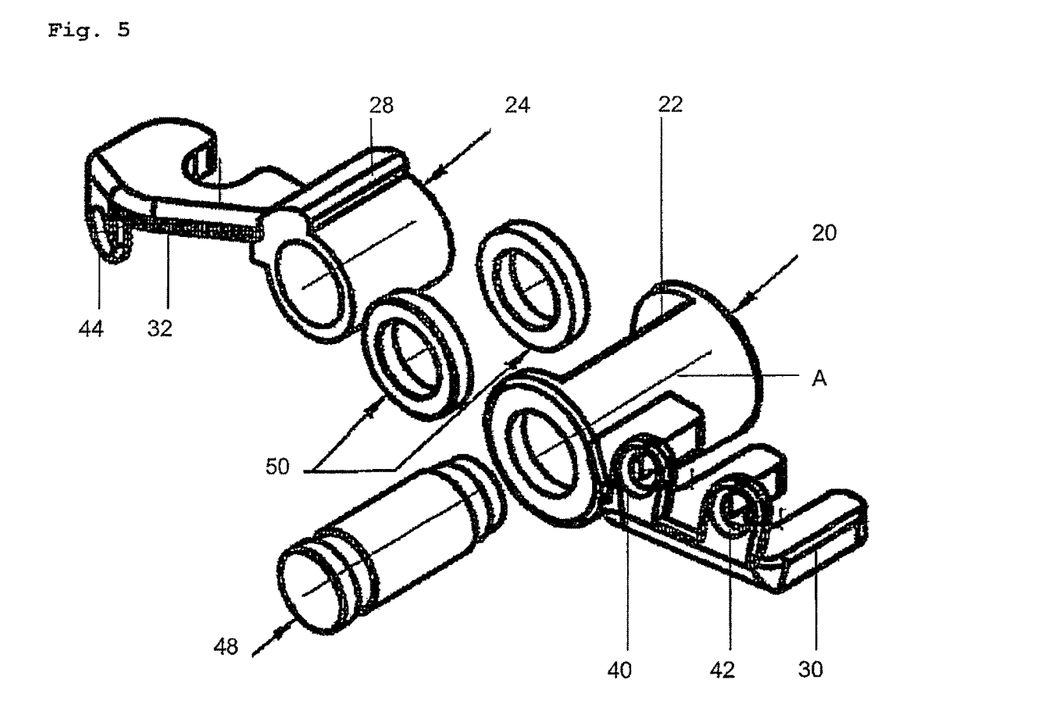
FIG. 5 is an exploded view of a hinge which is preferably to be used.

FIG. 5 shows an exploded view of the finger joint prosthesis with the hinge that is preferably to be used. The first joint element preferably includes an outside hollow cylinder 20 which has an insertion opening 22 on one side from the axis A. The inside hollow body 24 of the second joint element can be rotatably inserted into that insertion opening 22 of the outside hollow body 20, the insertion opening 22 extending over half of the peripheral surface of the cylinder. Formed on the inside hollow body 24 of the second joint element, on the outside thereof, is an abutment 28 which extends approximately over an angular portion of 90° and which forms the abutment edges of the inside hollow cylinder 24, for abutting against the inside edges of the insertion opening 22 of the outside hollow cylinder 20. The adjustable angular range can be implemented or limited as desired by the abutment 28 being of a suitable configuration.

Figure 6:
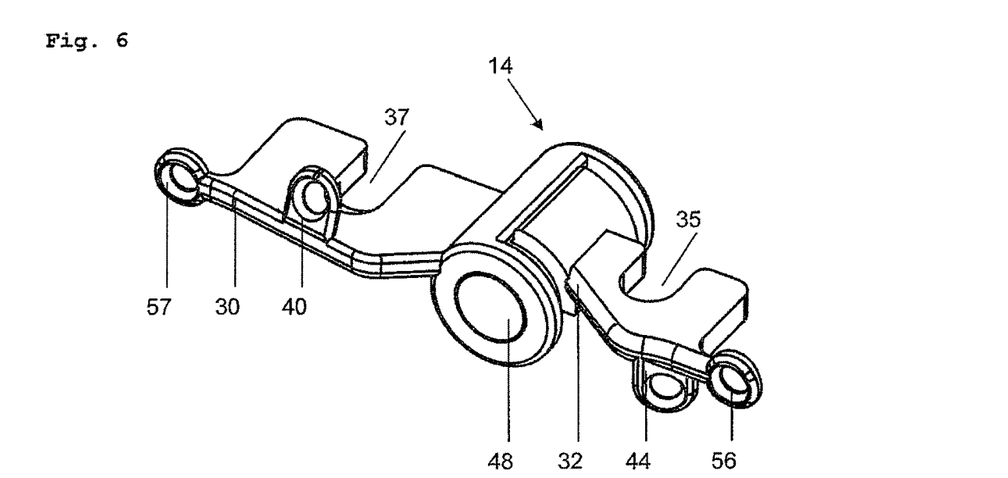
FIG. 6 is a perspective view of a finger joint prosthesis according to a fourth preferred embodiment of the present invention, wherein the end securing element on the distal and also the proximal anchoring bars is in the form of a securing eye.

FIG. 6 shows a perspective view of a further preferred embodiment of the assembled finger joint prosthesis. The end securing element is preferably in the form of a securing eye 57 and is disposed at the end of the proximal anchoring bar 30. The proximal anchoring bar 30 preferably has a lateral proximal securing eye 40 with recess 47. In this preferred embodiment, the end securing element is also in the form of a securing eye 56 at the end of the distal anchoring bar 32. The distal anchoring bar 32 also has a lateral proximal securing eye 44 with recess 35.

Figure 7:
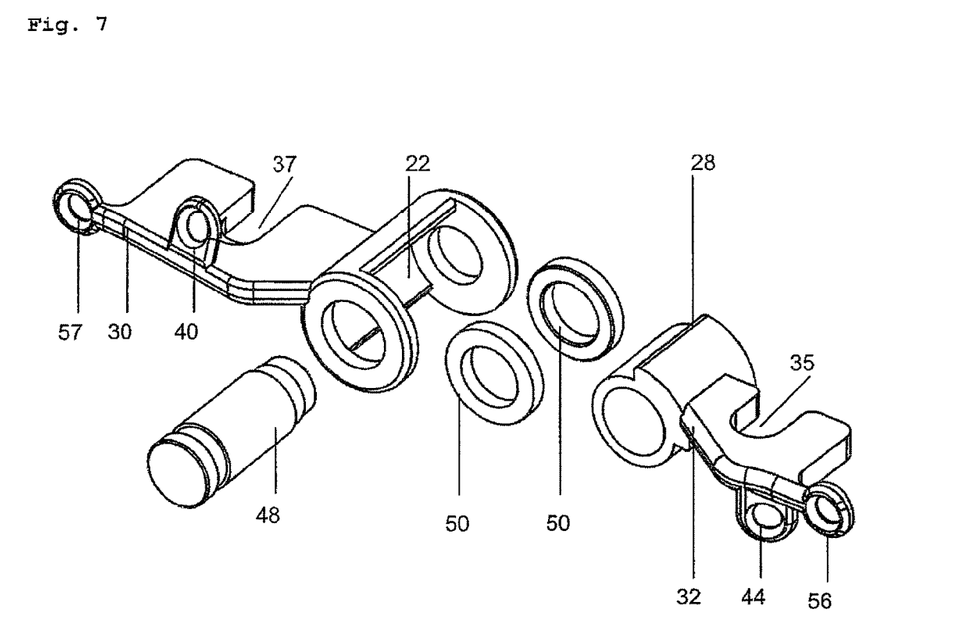
FIG. 7 is a perspective view of the finger joint prosthesis of FIG. 6.

FIG. 7 shows an exploded view of the finger joint prosthesis of FIG. 6 with a hinge as shown in FIG. 5.

Figure 8:
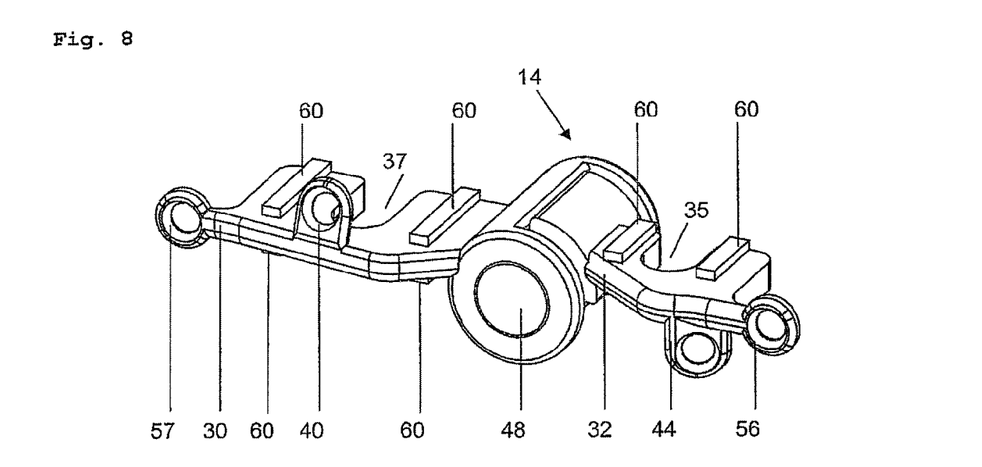
FIG. 8 is a perspective view of the finger joint prosthesis of FIG. 6 having eight ribs of rectangular cross-section.
Figure 9:
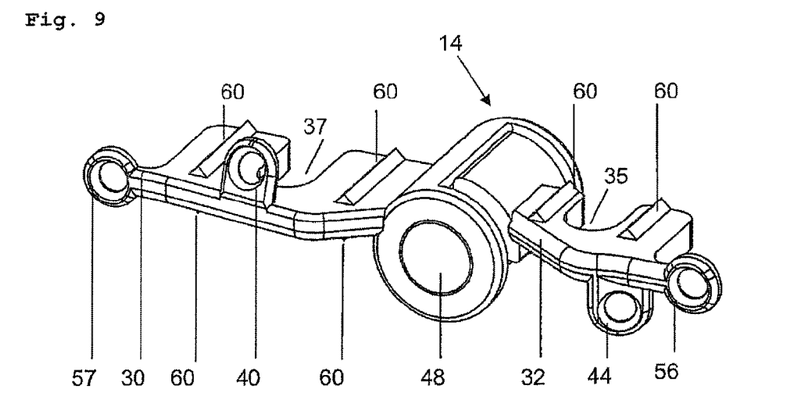
FIG. 9 is a perspective view of the finger joint prosthesis of FIG. 6 having eight ribs of triangular cross-section.
Figure 10:
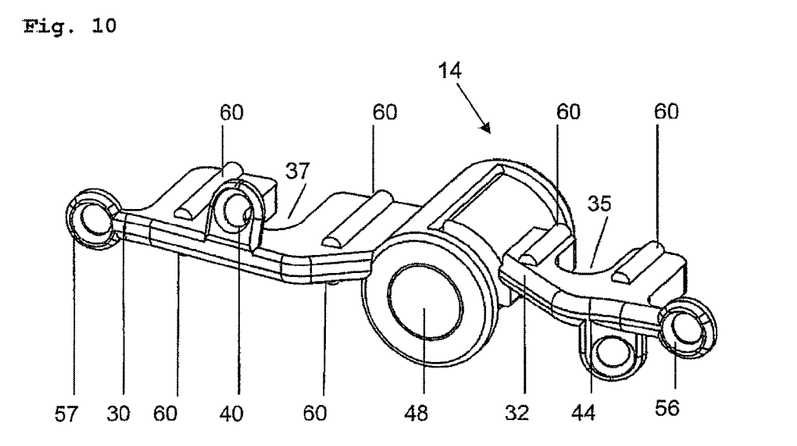
FIG. 10 is a perspective view of the finger joint prosthesis of FIG. 6 having eight ribs having a cross-section in the form of a semicircle.

FIGS. 8, 9 and 10 show preferred embodiments by way of example of a finger joint prosthesis as shown in FIG. 6 with eight ribs 60. The cross-section in this case is preferably rectangular, triangular and in the form of a semicircle. Growth to the bone and the stability of the finger joint prosthesis are improved by the ribs.

Figure 11:
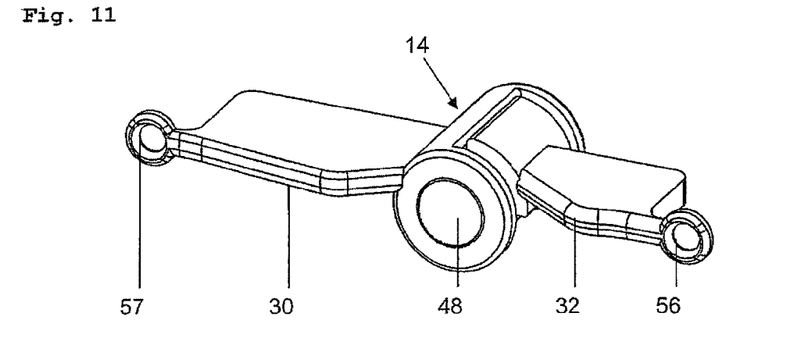
FIG. 11 is a perspective view of a finger joint prosthesis according to a fifth preferred embodiment of the present invention with exclusively two end securing eyes.

FIG. 11 shows a preferred embodiment of a finger joint prosthesis having a hinge as shown in FIG. 5, but with exclusively two end securing eyes. As illustrated no recesses are necessary or provided.

Figure 12:
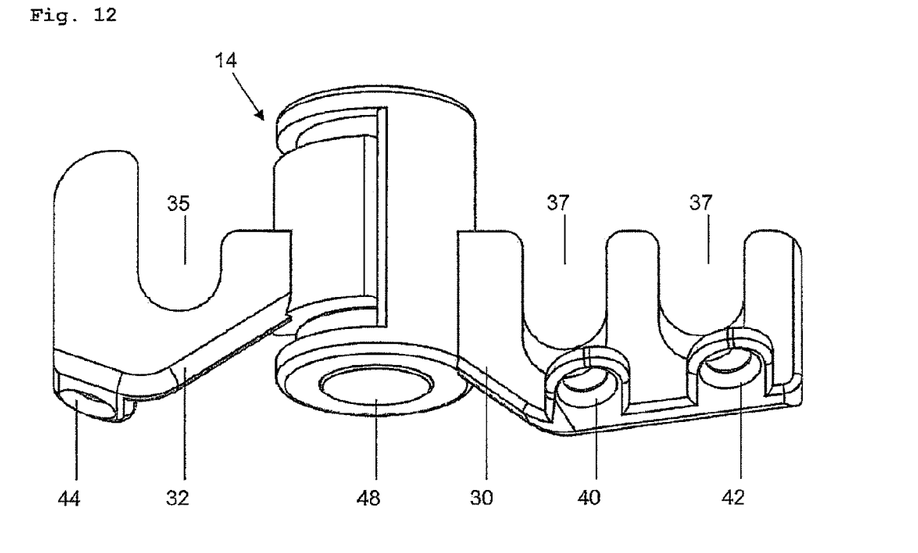
FIG. 12 is a perspective view of the finger joint prosthesis according to a sixth preferred embodiment of the present invention with exclusively lateral proximal securing eyes and an end securing element which is in the form of a wing-like widening of the distal anchoring bar in the horizontal direction and perpendicularly to the finger center line.

FIG. 12 shows a preferred embodiment of a finger joint prosthesis as shown in FIG. 5 with exclusively lateral proximal securing eyes and an end securing element. The latter is in the form of a wing-like widening of the distal anchoring bar in a horizontal direction and perpendicularly to the finger center line and in installation projects beyond the finger center line. As a result the end securing element reduces unfavorable lever effects. It is possible in that way to preclude fatigue fractures. The end of the wing-like widening, that engages into the bone, is rounded off. At the front end the widening terminates flush with the anchoring bar.

Figure 13:
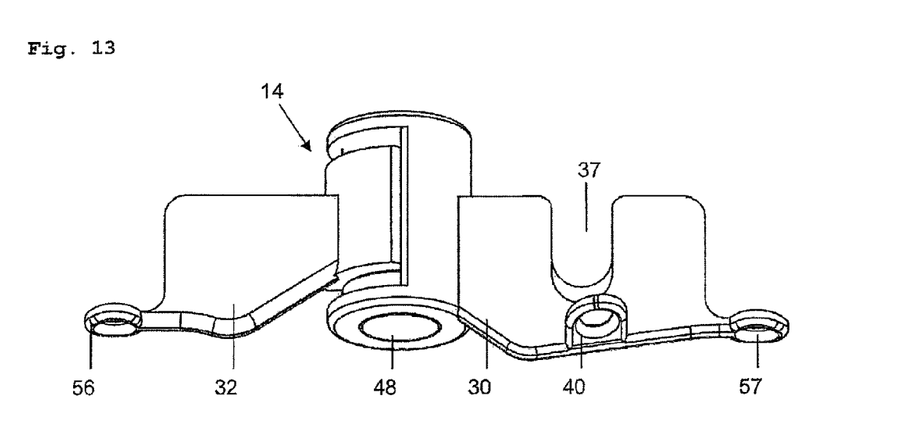
FIG. 13 is a perspective view of the finger joint prosthesis of FIG. 11 with an additional lateral proximal securing eye with recess on the proximal anchoring bar.

FIG. 13 shows a preferred embodiment by way of example of a finger joint prosthesis as shown in FIG. 11, wherein a lateral proximal securing eye 40 together with corresponding recess 37 is provided at the proximal anchoring bar 30.

A proximally extending flat anchoring bar 30 is shaped in one piece at the end on the outside peripheral surface of the outside hollow cylinder 20. That proximal anchoring bar 30 extends from the rear side of the outside hollow cylinder 20 approximately to the center thereof. The proximal anchoring bar 30 defines a surface extending transversely relative to the axis A of the joint body 14. The height of the proximal anchoring bar is about one quarter of the total length of the joint body 14. As can be seen from FIG. 2 the proximal anchoring bar 30 is shaped on the outside peripheral surface of the outside hollow cylinder 20 somewhat above a notional horizontal plane extending through the axis center point.

As shown in FIG. 5 a distal anchoring bar 32 extending from the rear side to approximately the center of the abutment 28 is integrally formed on the inside hollow cylinder 24 in a plane with the proximal anchoring bar 30. The distal anchoring bar 32 extends distally outwardly from the inside hollow cylinder 24 and is also of an areal configuration.

Those anchoring bars 30, 32 are therefore of an areal configuration to carry the forces acting in the anchoring bars 30, 32. The distal anchoring bar 32 can be pivoted upwardly through about 90 degrees in relation to the proximal anchoring bar 30, from the implantation position shown in the figures.

When using lateral proximal securing eyes 40, 42 and 44 they are so arranged on the proximal and distal anchoring bars 30, 32 that they are disposed in the region of the recesses 35, 37 in such a way as to also permit the fixing screws to be screwed inclinedly into the openings of the lateral proximal securing eyes 40, 42 and 44. To permit the fixing screws to be screwed inclinedly into the lateral proximal securing eyes 40, 42 and 44 particularly well, slope portions 38 are provided on the anchoring bars 30, 32 in the region of the lateral proximal securing eyes 40, 42 and 44 at the apex points of the recesses 35, 37. The material thickness of the slope portions 38 increases in the direction of the lateral securing eyes, more specifically to the full material thickness of the anchoring bar of preferably between 0.7 and 1.3 mm. The lateral proximal securing eyes 40, 42 and 44 can further be inclined out of the vertical through between about 5 and 10 degrees in order to assist with inclinedly screwing in the fixing screws. The finger joint prosthesis according to the invention makes it possible to entirely or partially dispense with lateral proximal securing eyes.

The rear side (away from the bone in the installation position) of the proximal anchoring bar 30 extends from the rear side of the outside hollow cylinder 20 at an angle of about 45° rearwardly to an apex point and rises therefrom to the outer free end at a shallow angle. The limbs formed in that way of the anchoring bars 30, 32 include between them an obtuse angle which is preferably between 150 and 170 degrees in order in that way to adapt the anchoring bars to the natural geometry of the finger bone and to improve stability by increasing the contact surface area in the bone without limiting the mobility of the joint.

To relatively movably connect the first joint element to the second joint element, a spindle 48, preferably comprising polyethylene, is inserted through a front end opening in the end of the outside hollow cylinder 20, the spindle 48 passing through the cylindrical opening in the inside hollow cylinder 24 and thus fixing it in the outside hollow cylinder 20. The spindle 48 is non-detachably connected to the outside hollow cylinder 20 by selecting a suitable press fit between the spindle 48 and the outside hollow cylinder 20. At the front end the spindle 48 has a pin of reduced diameter, which can be pressed into the front end face of the outside hollow cylinder 20.

Annular disks 50, preferably of polyethylene are inserted to reduce friction between the end outsides of the inside hollow cylinder 24 which is made from titanium nitrate and the end insides of the outside hollow cylinder 20 which is also made from titanium nitrate.

For implantation of the finger joint prosthesis, after detachment of the corresponding collateral ligament, a bore is milled by means of a round milling cutter from the radial side at the location indicated by the central circle in the Figure. The center point of the bore corresponds to the center of rotation of the proximal and distal phalanges 4, 6 at the beginning of the pivotal movement of the distal phalanx 6 out of the extension position into the flexion position. The inside diameter and the height of the bore correspond to the outside diameter and the height of the joint body 14. After milling the bore a slot milling cutter is used to mill from the radial side two slots 52, 54 extending in the longitudinal central direction of the phalanges from the milled bore. In that case the shape of the slots 52, 54 corresponds to the geometry of the anchoring bars 30, 32.

After milling of the bore and the slots 52, 54 the finger joint prosthesis is introduced with its front end into the milled bore, wherein the anchoring bars 30, 32 are inserted into the slots 52, 54 until the lateral securing eyes 40, 42, 44 or, depending on the respective design configuration, the medial securing eyes 56, 57, bear against the finger bone. If cylinders 58, 59 are provided it will be appreciated that bores adapted to the diameter of the cylinder 58, 59 must also be provided. Then the anchoring bars 30, 32 are secured to the bone material of the corresponding proximal and distal phalanges 4, 6. That is effected by screwing in titanium screws, depending on the respective design configuration through the respective securing eyes 40, 42, 44, 56 and 57, into the bone material.

The components of the finger joint prosthesis are preferably made from metal, in particular titanium or titanium nitrite. That material has the advantage that a durable high level of implant stability is achieved by bone growing into the porous surface of the material. It is further conceivable for the surface of the material to be provided with a biocompatible coating which promotes such growth. For example hydroxyapatite is particularly advantageous.

To achieve suitable frictional pairing as between the spindle and the hollow bodies the spindle preferably comprises a material with a degree of hardness different from the material of the hollow bodies, which however together form a good frictional pairing. In the case of hollow bodies of titanium or titanium nitrite a spindle of plastic material has proven to be advantageous, in particular a spindle of ultra-high molecular polyethylene (UHMWPE). However, all other suitable material pairings with appropriate anti-friction properties can also be considered.

Depending on the size of the finger joint to be replaced the dimensions of the finger joint prosthesis are preferably in the following ranges:

| | |
|---|---|
| Diameter of the joint body: | Between 6 and 8 mm |
| Diameter of the spindle: | Between 3 and 4 mm |
| Length of the anchoring bars: | Between 4 and 8 mm |
| Thickness of the anchoring bars: | Between 0.7 and 1.3 mm |

The present invention has been described by reference to replacement of the finger middle joint by the finger joint prosthesis according to the present invention. In the same manner, the finger joint prosthesis can also be used to replace the end joints of the fingers, with suitable adaptation of the dimensions while retaining the size relationships. It is also possible to design the prosthesis for further joints. For that purpose it is appropriate that all edges of the prosthesis can be harmonically adapted to the respective bone. In that respect it is particularly desirable if the end securing element does not project medially or laterally in the bone. Particularly preferably the end securing element projects 0.2 mm from the plane of the anchoring bar.

The subject-matter of the present invention can be seen not only from the subject-matter of the individual claims, but also from the combination of the individual claims with each other. All details and features disclosed in the documents, including the Abstract, in particular the spatial configurations shown in the drawings, are claimed as essential to the present invention insofar as they are novel individually or in combination over the state of the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A finger joint prosthesis comprising:
   a joint body (14) having first and second joint elements (20, 24) pivotably connected about an axis of rotation (A), the first joint element (20) having an external hollow cylindrical body with an insertion opening at one side thereof, the second joint element (24) having an internal hollow cylindrical body;
   an anchoring bar (30, 32) extending distally outwardly from each of the first and second joint elements (20, 24) and configured to be fixed to a proximal and a distal phalanx, the anchoring bars (30, 32) defining a horizontal plane for sliding into horizontal planar slots of a finger, each anchoring bar (30, 32) having a first side thereof, perpendicular to the axis of rotation (A), including one or more securing eyes (40, 42, 44) extending transversely to the horizontal plane of the anchoring bars (30, 32), and having an opposing second side thereof, perpendicular to the axis of rotation (A), free of securing eyes for horizontal advancement into the planar slots, each securing eye (40, 42, 44) including an opening for receiving fixing screws therein; and
   an end securing element extending distally from a distal end of at least one of the anchoring bars (30, 32), and medially disposed relative to the horizontal plane of the anchoring bars (30, 32),
   wherein in an installation position of the finger joint prosthesis, the internal hollow cylindrical body is inserted into the external hollow cylindrical body and a spindle is inserted into the internal hollow cylindrical body, the internal hollow cylindrical body being rotatable with respect to the external hollow cylindrical body, and
   wherein the finger joint prosthesis is configured to be horizontally implanted into a bore produced in a finger joint and each of the anchoring bars is configured to be horizontally inserted into the slots which extend longitudinally relative to the proximal and distal phalanges.

2. The finger joint prosthesis as set forth in claim 1 wherein the end securing element is provided in a horizontal direction, perpendicularly to a finger center line, in the form of a widening of the at least one anchoring bar (30, 32).

3. The finger joint prosthesis as set forth in claim 1 wherein the end securing element is an end securing eye (56, 57).

4. The finger joint prosthesis as set forth in claim 3 wherein the end securing element comprises at least two adjacent securing eyes.

5. The finger joint prosthesis as set forth in claim 1 wherein the end securing element is a cylinder (58, 59).

6. The finger joint prosthesis as set forth in claim 1 wherein the end securing element comprises a cylinder (58, 59) and a securing eye (56, 57).

7. The finger joint prosthesis as set forth in claim 1 wherein a surface of the end securing element is of a rough nature to promote improved growth to the bone.

8. The finger joint prosthesis as set forth in claim 1 wherein at least one rib (60) is provided at a flat side of at least one of the anchoring bars (30, 32).

9. The finger joint prosthesis as set forth in claim 1 wherein the internal hollow cylindrical body includes an abutment (28) extending radially outwardly from a remainder of the internal hollow cylindrical body, the abutment (28) restricting motion between the first and second joint elements (20, 24).

* * * * *